United States Patent
Hallemeier et al.

(10) Patent No.: US 11,990,217 B2
(45) Date of Patent: *May 21, 2024

(54) HEALTHCARE COVERAGE MATCHING AND VERIFICATION

(71) Applicant: Health Management Systems, Inc., Irving, TX (US)

(72) Inventors: Eric Hallemeier, Dallas, TX (US); Deb Grier, Delanson, NY (US); Gopi Kolla, Irving, TX (US); Anand Padmanaban, Lewisville, TX (US); Chris Lolo, McKinney, TX (US); Karthik Sundaram, Little Elm, TX (US); Kevin Nyaribo, Irving, TX (US)

(73) Assignee: Health Management Systems, Inc., Irving, TX (US)

( * ) Notice: Subject to any disclaimer, the term of this patent is extended or adjusted under 35 U.S.C. 154(b) by 426 days.

This patent is subject to a terminal disclaimer.

(21) Appl. No.: 17/240,600

(22) Filed: Apr. 26, 2021

(65) Prior Publication Data

US 2021/0391045 A1    Dec. 16, 2021

Related U.S. Application Data

(63) Continuation of application No. 16/181,778, filed on Nov. 6, 2018, now Pat. No. 10,991,457.

(Continued)

(51) Int. Cl.
*G16H 70/20* (2018.01)
*G06Q 40/08* (2012.01)
(Continued)

(52) U.S. Cl.
CPC ............. *G16H 15/00* (2018.01); *G06Q 40/08* (2013.01); *G16H 10/60* (2018.01)

(58) Field of Classification Search
CPC ........ G16H 15/00; G16H 10/60; G16H 40/20; G06Q 40/08
See application file for complete search history.

(56) References Cited

U.S. PATENT DOCUMENTS

| 7,720,691 B2 | 5/2010 | Hasan |
| 2004/0128165 A1 | 7/2004 | Block |

(Continued)

*Primary Examiner* — Maroun P Kanaan
(74) *Attorney, Agent, or Firm* — Perkins Coie LLP

(57) ABSTRACT

Disclosed are systems, methods and devices for providing healthcare coverage matching and verification. In some aspects, a method includes receiving, from a frontend graphical user interface (GUI), a healthcare coverage application comprising client demographics that include at least two of the following: a last name, a first name, a birthdate, an identification number, an address and a request type associated with a client, using a parallel matching and verification architecture to determine, based on a first set of criteria, a matching database record from an eligibility database that corresponds to the healthcare coverage application, and communicate with a healthcare provider using electronic data interchange transactions, identify, based on a second set of criteria, a medical policy that corresponds to the matching database record, and verify the medical policy, and transmitting, to the frontend GUI, the medical policy to allow reception of the medical policy by the client.

25 Claims, 12 Drawing Sheets

Related U.S. Application Data

(60) Provisional application No. 62/582,255, filed on Nov. 6, 2017.

(51) Int. Cl.
   *G16H 10/60*       (2018.01)
   *G16H 15/00*       (2018.01)

(56) References Cited

U.S. PATENT DOCUMENTS

| | | |
|---|---|---|
| 2012/0316898 A1 | 12/2012 | Levitt |
| 2018/0358116 A1* | 12/2018 | Kristin ............. G08G 1/096855 |
| 2019/0096534 A1* | 3/2019 | Joao ........................ G16H 10/60 |
| 2019/0098492 A1* | 3/2019 | Shalayev .............. H04W 12/03 |

* cited by examiner

| Field Name | DESCRIPTION |
|---|---|
| Medicaid ID | 20 digit number to map between request file and result file |
| APP TYPE | fixed value |
| MEMBER LAST NAME | last name of the member in question |
| MEMBER FIRST NM | first name of the member in question |
| MEMBER SSN NUM | |
| MEMBER BIRTH DT | |
| COVERAGE_TYPE_CD | MMED, RX, DENT |
| EVENT_TYPE_CD | 01, 02, 03, 04 |
| REQUEST_TYPE_CD | 01, 02, 21, 22 |
| Medicaid Start Date | |
| Medicaid Stop Date | |
| PAID_AMT | Value is decimal 9,2 |
| PROVIDER_ID | |
| POLICY_TYPE_CD | MCAID, MCA, MCB |
| MEMBER_ID_QUAL_CD | |

FIG. 9A

| Field Name | DESCRIPTION |
|---|---|
| MA_NUMBER | State Medicaid Number |
| CARRIER_CD | HMS Insurance Carrier Code (5 Digits) |
| CARRIER_NM | HMS Insurance Carrier Name |
| GROUP_NUMBER | Insurance Group # |
| POLICY_NUMBER | Insurance Policy # |
| VERIFY_DT | MM/DD/YYYY FORMAT |
| PH_LAST_NAME | Subscriber Last Name |
| PH_FIRST_NAME | Subscriber First Name |
| RELATIONSHIP_CD | Patient Relationship to Subscriber |
| RECIP_LAST_NAME | Patient Last Name |
| RECIP_FIRST_NAME | Patient First Name |

FIG. 9B

HEALTHCARE COVERAGE MATCHING AND VERIFICATION

CROSS-REFERENCE TO RELATED APPLICATIONS

This application is a continuation of and claims the benefit of priority of U.S. application Ser. No. 16/181,778 entitled "HEALTHCARE COVERAGE MATCHING AND VERIFICATION" and filed Nov. 6, 2018, which claims the benefit of priority U.S. Provisional Patent Application 62/582,255 entitled "SYSTEMS, DEVICES AND METHODS FOR PROVIDING IMPROVEMENTS WITH HEALTH CARE OUTCOMES AND COSTS" and filed on Nov. 6, 2017. The entire content of the before-mentioned patent application is incorporated by reference as part of the disclosure of this patent document.

TECHNICAL FIELD

This patent document relates to methods, systems and devices for health information technology.

BACKGROUND

The healthcare system of the United States is a complex network of various types of organizations including private and public healthcare facilities and insurance providers. For example, U.S. healthcare facilities are mostly owned and operated by private sector businesses, yet most healthcare spending has been paid for through government-funded insurance programs like Medicare, Medicaid, Children's Health Insurance Program (CHIP) and Veterans Health Administration (VHA). Despite the diversity, healthcare outcomes are mixed. While the U.S. is considered to have some of the world's best doctors, hospitals, and procedural and treatment options, the United States ranks 42nd among 224 nations (and 22nd out of the 35 industrialized OECD countries) in life expectancy, and ranks relatively low among other developed nations on a wide range of other healthcare quality metrics.

The diversity and complexity of the U.S. healthcare system is rooted in decisions made as early as World War I. In those earlier years, insurance policies were conceived and implemented in a way that was largely divorced from government involvement in the payment of health care, from which a varied system of private insurance emerged. While the private system that developed over the years was suitable for families who received health insurance through their employers, publicly-funded and administered systems were created in the 1960s—e.g., Medicare and Medicaid—to help cover retired individuals and others who were not adequately covered by the private insurance system. Given the well-publicized increases in healthcare spending that have occurred in the United States over the last 50 years, both the private sector and state and federal governments have continually innovated new systems and processes to improve healthcare outcomes for patients, as well as to better coordinate the proper allocation of coverage and appropriate sharing of costs between health care payers. Nevertheless, healthcare costs continue to rise, and if not adequately controlled in the future, could one day exceed sustainable levels.

SUMMARY

Disclosed are systems, methods and devices that include databases communicatively connected to matching engine components comprising matching APIs and post-match APIs, real-time or near real-time processing components, as well as verification components and APIs that provide significant improvements in processing and managing healthcare information, with superior healthcare outcomes and cost savings to patients, consumers, providers, payers and the United States government.

In one exemplary aspect, the disclosed technology may be used to provide a method for healthcare coverage matching and verification. This method includes receiving, from a frontend graphical user interface (GUI), a healthcare coverage application comprising client demographics that include at least two of the following: a last name, a first name, a birthdate, an identification number, an address and a request type associated with a client, using a parallel matching and verification architecture to determine, based on a first set of criteria, a matching database record from an eligibility database that corresponds to the healthcare coverage application, and communicate with a healthcare provider using electronic data interchange transactions, identify, based on a second set of criteria, a medical policy that corresponds to the matching database record, and verify the medical policy, and transmitting, to the frontend GUI, the medical policy to allow reception of the medical policy by the client.

In yet another exemplary aspect, an apparatus comprising a memory and a processor implements the above-described methods is disclosed.

In yet another exemplary aspect, the method may be embodied as processor-executable code and may be stored on a non-transitory computer-readable program medium.

The above and other aspects and features of the disclosed technology are described in greater detail in the drawings, the description and the claims.

BRIEF DESCRIPTION OF THE DRAWINGS

FIGS. 9A and 9B illustrate example request and response parameters, respectively.

DETAILED DESCRIPTION

Figure 1:
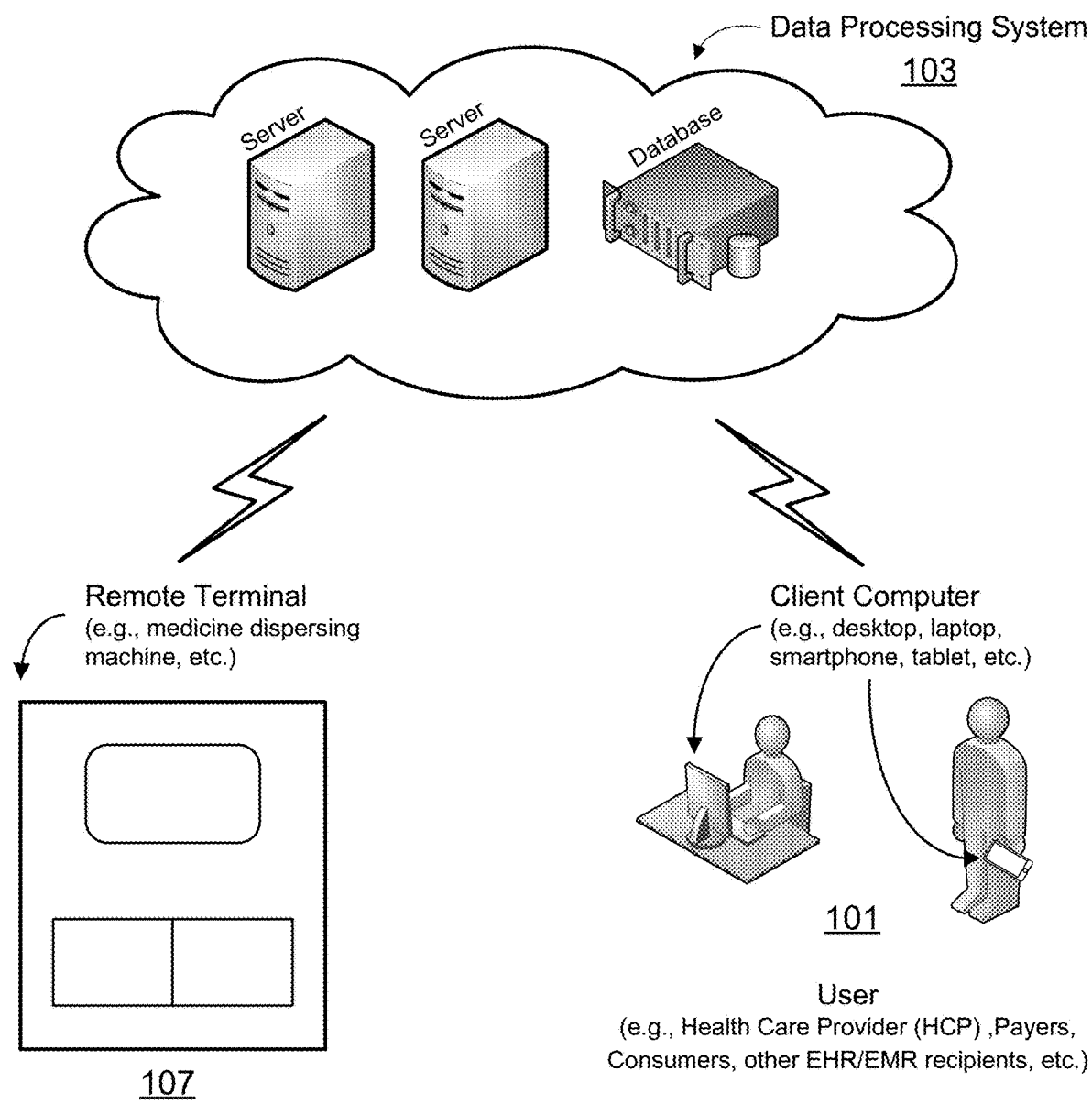
FIG. 1 illustrates an exemplary embodiment of a healthcare cost management system in accordance with the presently disclosed technology for providing healthcare coverage matching and verification, resulting in improvements in healthcare outcomes and costs to patients, consumers, providers, payers and/or the United States government.

In the following description, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

Medicaid is a government-funded insurance program designed to provide healthcare coverage to individuals in the United States that fall into certain categories typically based on low income or disabilities. It has been estimated that Medicaid spending represents $1 out of every $6 spent on healthcare in the United States. Medicaid is jointly funded by the federal government and state governments, but is managed by the states, and as a result, funding and eligibility rules vary widely from state-to-state. For example, each state runs its own version of Medicaid, with slightly different rules and coverage.

In every state, the Medicaid program must cover basic medical care, which includes, for example, inpatient hospital care, physician services, outpatient hospital or clinic care, laboratory and X-ray imaging services, prescription drugs, and other basic healthcare services. However, the different state Medicaid programs differ on other (optional) medical services to cover, either partially if at all, such as preventative screenings, physical therapy, eye examinations, hearing tests, dental care, and others. Also, states can establish their own Medicaid provider payment rates within requirements set by the federal government. States generally pay for services through fee-for-service or managed care arrangements. For example, under fee-for-service arrangements, states pay healthcare providers (e.g., physicians, healthcare facilities, etc.) directly for services performed for the patient, in which the decided payment rates are based on (i) the cost of providing the service, (ii) analysis of what commercial payers pay in the private market, and (iii) a percentage of what Medicare pays for equivalent services. For example, under managed care arrangements, states contract with organizations to deliver care through networks and pay providers. Notably, approximately 70% of Medicaid enrollees are served through managed care delivery systems, where providers are paid on a monthly capitation payment rate.

Some Medicaid beneficiaries have one or more sources of health insurance coverage, also referred to as third party liability. Third party liability (TPL) refers to the legal obligation of third parties (e.g., certain individuals, entities, insurers, or programs) to pay part or all of the expenditures for medical assistance furnished under a Medicaid state plan. Administration of a Medicaid plan in a state typically involves a "coordination of benefits" (COB) in determining what benefits apply for particular provider services and who and how much TPL is to be assigned to cover payment for such services. COB refers to activities involved in determining Medicaid benefits when an enrollee has coverage through an individual, entity, insurance, or program that is liable to pay for healthcare services. Individuals eligible for Medicaid assign their rights to third party payments to the State Medicaid agency. Examples of third party payers who may be liable, e.g., TPLs, include group health plans, self-insured plans, Medicare (e.g., if Medicaid beneficiary qualifies for this separate government program), managed care originations, pharmacy benefit plans and organizations, among others.

Despite this organization, there are many complications and inefficiencies in the reimbursement of healthcare providers for the services they provide to their patients. For example, the Medicaid system does not provide a framework for providers to know the full extent of coverage a particular patient may have for any given service. As such, the healthcare provider may make a particular decision for the patient (e.g., provide a service) without knowing how much he/she would be reimbursed or whom the primary reimbursement should come from. In addition, coordination of the payment of patient benefits with the correct payer before Medicaid makes payments on behalf of a patient is far more efficient and cost-effective for the Medicaid system than when Medicaid is forced to "chase" reimbursement of payments with that payer after Medicaid pays first.

The present document uses examples from Medicaid and its patients only to facilitate understanding, and the disclosed techniques and embodiments may be practiced in other systems and frameworks that use different providers and consumers. For example, embodiments of the disclosed technology are equally applicable to Medicaid to commercial, commercial to commercial, Medicare to commercial, Charity Care and the like. In addition, payment processing examples provided in the context of Medicaid are equally applicable to other entities across the healthcare continuum (e.g., enrollment, adjudication, point of services, billing, other third part liability, etc.) to ensure that the healthcare system is appropriately billed upon the required services being provided to the consumer (or recipient, or client).

Disclosed are computing systems, methods and devices include databases communicatively connected to matching engine components comprising matching and post-match APIs, real-time or near real-time processing components, as well as verification components and APIs that are arranged in specific configurations to effectively receive and process medical information and to provide improved results that are accessible in real-time or near real-time and providing improved healthcare outcomes and cost savings to patients, providers and payers using healthcare service data matching and verification techniques. In some implementations in accordance with the present technology, the disclosed methods, systems and devices can provide increased cost savings, ensure Medicaid maintains payer of last resort status, and reduce provider abrasion through transactional matching and verification.

The disclosed computing architectures enable transactional matching and verification (TMV) that provides real-time or near real-time match and verification of Medicaid recipients to other coverage, e.g., as an alternative to traditional cyclical batch processes. TMV provides an end user, e.g., including a human or a machine end user, a single application for identifying other coverage across payers, e.g., within the US for medical and pharmacy plans. The example TMV application can be implemented using the systems, devices and methods described herein, for example, to serve a variety of consumers at strategic points in the healthcare continuum, including but not limited to, Point of Billing, Point of Service, Point of Prior Authorization, Point of Medicaid Enrollment, and State and Federal Exchange Enrollment.

In some embodiments, a healthcare management system for providing improvements with healthcare outcomes and costs includes a data processing system in communication with client computing devices to provide third party liability (TPL) and eligibility verification for patients insured under a particular program or plan, such as Medicaid programs. In some implementations, the data processing system includes multiple subsystems including a batch capability subsystem, a real-time or near real-time capability subsystem, a matching service subsystem and a verification service subsystem that processes patient and insurance information to, among other things, automatically determine payment eligibility information, and provide recommendations for medical providers.

In some embodiments, the results of the matching and verification processes may be retrieved from a decentralized record management system using blockchain technology. In an example, the blockchain does not store the raw medical data or records, but rather data pointers (or more specifically, hashed data pointers) that indicate where the records are available. Thus, embodiments of the disclosed technology can securely access the blockchain ledger to determine which healthcare database to access in order to provide matching and verification results.

In some embodiments in accordance with the present technology, a healthcare management system includes one or more computers of the data processing system in communication with the client computer, e.g., via a communication network or link, such that the data processing system is configured to receive, from the client computer, healthcare information associated with medical and pharmacy coverages, benefits, and/or claims data associated with a patient enrolled in a Medicaid program; determine one or more instances ascribable to another coverage type (e.g., a coverage, an overpayment, an eligibility for coverage, or an eligibility for a qualified life event) by matching the data with data records in a patient eligibility database; and generate an output associated with the determined instance(s) ascribable to the other coverage types.

In some implementations of the healthcare management system, the system is configured to identify the one or more instances ascribable to the other coverage (e.g., held or available to the patient) and verify the identified instance(s) ascribable to the other coverage, e.g., through communication to the entity corresponding to the other coverage. In some implementations of the healthcare management system, the data processing system is configured to validate an accuracy of the matching based on specific criteria. In some implementations, the data processing system is configured to verify the identified other coverage and/or eligibility by automatically contacting an insurance provider associated with the identified other coverage held or available to the patient and confirming one or both of eligibility of the patient for coverage (e.g., such as a payment or future payment of a claim).

In some implementations, the determined amount of insurance coverage includes a plurality of options associated with the healthcare service to achieve substantially the same healthcare outcome. For example, the healthcare service can include a prescription drug, and the plurality of outcomes can include an amount associated with a name brand drug and an associated generic drug. In such implementations, for example, the healthcare management system can further include a remote terminal in communication with the data processing system (or in some implementations, in communication with the client computer) and operable to perform a service for a user at the location of the remote terminal, such as, for example, dispense medical treatment products including one or more of a medical device or a pharmaceutical drug. For example, in such implementations, the generated output of the data processing system can include a command to be transmitted to the remote terminal to dispense a particular product stored in the remote terminal, in which the remote terminal processes the command to select a product among the medical treatment products based on the determined amount of insurance coverage, and to dispense the selected product.

Embodiments of the disclosed technology are more generally application to matching and verification with a healthcare backend (with an architecture implemented and provided by a healthcare provider, the government, medical establishments, etc.) and a recipient (or consumer)-facing application, which may be configured to accept an inquiry through a frontend graphical user interface (GUI) and provide a response through the same GUI, based on a valid and secure identification of the consumer (or recipient).

FIG. 1 illustrates an example embodiment of a healthcare cost management system in accordance with the present technology for providing healthcare coverage matching and verification, resulting in improvements in healthcare outcomes and costs to patients, providers and/or payers. The system includes a data processing system 103 including one or more computing devices in a computer system or communication network accessible via the Internet (e.g., referred to as "the cloud" or "on premise"), e.g., including servers (e.g., virtual servers) and/or databases in the cloud and physical infrastructure inside a facility of the healthcare management service entity. In some implementations, the computing devices of the data processing system include one or more servers in communication with each other and one or more databases. The data processing system is in communication with a client computer 101, e.g., operated by a client user such as a healthcare provider (HCP) and/or a health insurance representative, to receive and transfer data from/to the data processing system, to display data, and/or to manage some processing and storage of the data. In implementations, for example, data communications between the client computer and the one or more computing devices of the data processing system use various communication protocols such as HTTP, HTTPS, FTP, SFTP etc. over wired or wireless network technology such as LTE, Wi-Fi or others.

In some embodiments, for example, the system can include a remote computing terminal 107 to implement various outputs of the system to provide a particular healthcare outcome or cost management service. In some embodiments, the remote computing terminal can include a computerized kiosk in communication with the data processing system operable to dispense a particular medical treatment device or substance to an end user, such as a patient. For example, the kiosk can include a pharmaceutical dispensing machine that securely stores various pharmaceutical products, such as in a clinic or hospital, where data received by the data processing system can cause the kiosk to dispense a particular product to the end user. In some implementations, for example, the remote computing terminal is in communication with the client computer and operates with an application of the system (e.g., an app or API) on the client computer in a Point of Service system to carry out operations for the healthcare provider, the patient, or other user, such as for example, dispensing medical treatment products.

The system includes a customized application program interface (API) operable on the client computer to provide data management for providing input data to the data processing system and to implement various functionalities. The API includes program code that is stored in the memory of the client computer and executable by a processor of the client computer to control the operations of the client computer to implement various processes of present technology. The API manages the aggregation and transfer of input data from the client computer, such as data associated with the member/patient's healthcare coverage. In some implementations, the data can include patient health data and/or provider notes (e.g., diagnoses, treatment options, prescriptions, etc.).

In some implementations, for example, the API portion of the system can be used for transactional passing of information and/or it can be attached to a front-end application. The front-end application includes a user interface (UI) that enables the client user of the client computer to do one-time lookups on their Medicaid recipients, e.g., in real-time or near real-time. Implementation of the system using the API can provide efficient data processing by enabling multiple products/systems to acquire information from a single source.

In some implementations, the UI supports entry of Medicaid recipient demographics and/or other information for a patient to determine whether the Medicaid recipient possesses and/or is eligible for other coverage, e.g., healthcare insurance coverage outside of the state's Medicaid program. For example, the Medicaid recipient demographics can include the Medicaid member name, address, date of birth, Social Security number, gender, Medicaid member ID, and/or other data elements. The UI supports return of a Medicaid recipient's other coverage information determined by the data processing system. For example, the return can include primary coverage information that may include commercial plan, policy ID, date of service verified, group number, a carrier code, and/or a carrier name. The UI can provide the client user with information in a single iteration, and is flexible for client customization, such as via ON/OFF controls for such features. The UI of the front-end application can include security and authentication requirements built in. The UI of the front-end application can provide admin rights that are managed by the client and/or a representative associated with the data processing system, which can be given global authority to modify/remove client access. The UI can provide access logs to identify fraudulent use. On the back-end of the application, credentials to UI activity are matched, e.g., for security purposes.

Implementations of the data processing system in communication with the client computer, client application and/or remote computing terminal include one or more of the following features. For example, the system can be implemented to verify TPL and/or eligibility information associated with Medicaid enrolled members or potential members. In some examples, member inquiries can be vetted (e.g., "scrubbed") for multiple instances from the same provider within a predetermined range. Multiple inquiries can be omitted from the verification process unless different information is provided or a new TPL flag is generated. Input data from the client computer can include coverage files (e.g., client other coverage files), which can be broken out for verifications (e.g., auto/manual) and distributed to the client in a single comprehensive file. Client other coverage files may include timestamps for "received" and "returned" statuses. For example, the system can provide audits conducted on a periodic, or otherwise ongoing, basis to ensure process efficiency and quality.

In some implementations, automated verifications are utilized in validating the quality of other coverage data given to clients in real-time or near real-time. The system supports verification via API and UI delivery methods. In example implementations, the API/UI can return match and verified responses to the client computer in real-time or near real-time, e.g., average response time ranging between 8 to 15 seconds. The system can be implemented to assess and quantify a new client impact on verifications, including identification of anticipated member volume.

The following is an example implementation that can be performed by the example healthcare cost management system. For example, a healthcare provider treats a Medicaid patient, e.g., in healthcare facility, home of the patient or other. The healthcare provide submits information associated with the patient, such as Medicaid coverage information of the patient known to the healthcare provider. In some implementations, the healthcare provider can submit a Medicaid-only patient list to the data processing system, e.g., which can be periodically such as on a daily schedule or intermittently. Upon receiving the submitted information, the data processing system matches the patient to with data records in a patient eligibility database, included and/or in communication with the data processing system, to determine one or more instances ascribable to another coverage that pertains to the patient. The data processing system, in some implementations, can verify the other coverage. The data processing system returns the matched (and, in some implementations, verified) other coverage data to the healthcare provider. In some implementations that include a list of Medicaid-only patients, the data processing system returns the matched (and, in some implementations, verified) other coverage data of the provider's Medicaid patients to the healthcare provider.

For example, implementation of the method by the healthcare cost management system can assist healthcare providers (e.g., hospital providers, clinic providers, etc.) with accurately billing on the first time, e.g., with no added cost to the Medicaid program. The system can verify and communicate other primary coverage for Medicaid members before hospitals incorrectly bill claims to Medicaid, e.g., which is a win-win-win scenario for all stakeholders such as state Medicaid agencies, Medicaid healthcare providers, patients, etc. For example, state Medicaid agencies can benefit through enhanced cost savings by avoiding erroneous payments without incurring additional costs, and saving rework for the state; Medicaid providers can benefit by realizing potential higher payments from health plans for the payment of services to Medicaid recipients with other coverage, as well as a reduction in administrative burden stemming from state or health plan coordination of benefits/third party liability (COB/TPL) recovery solutions; and patients can benefit by receiving the full benefit of their health plan coverage through proper coordination of benefits and timely service authorizations. Additional benefits of implementations of the healthcare cost management system include support to states that contract with Managed Care Organizations (MCOs) for managing the intent of the COB/TPL requirements, e.g., often found in agreements between the state and the MCO.

Implementations of the disclosed healthcare cost management system and methods may contribute to a more sustaining healthcare system, including ensuring Medicaid remains the payer of last resort and improving the financial performance of the Medicaid program and its providers, while reducing administrative burden. For example, provider abrasion and frustration due to pay-and-chase activities may be reduced by the example system. Strategically distributing primary coverage data for Medicaid members to providers at the time of service and prior to billing can provide value to Medicaid TPL services. Implementations of the disclosed healthcare cost management system and methods can yield the most efficient use of that information, resulting in the maximization of Medicaid program cost savings, e.g., allowing for the potential enhancement of provider remuneration, while minimizing administrative hassles and costs for all.

Figure 2:
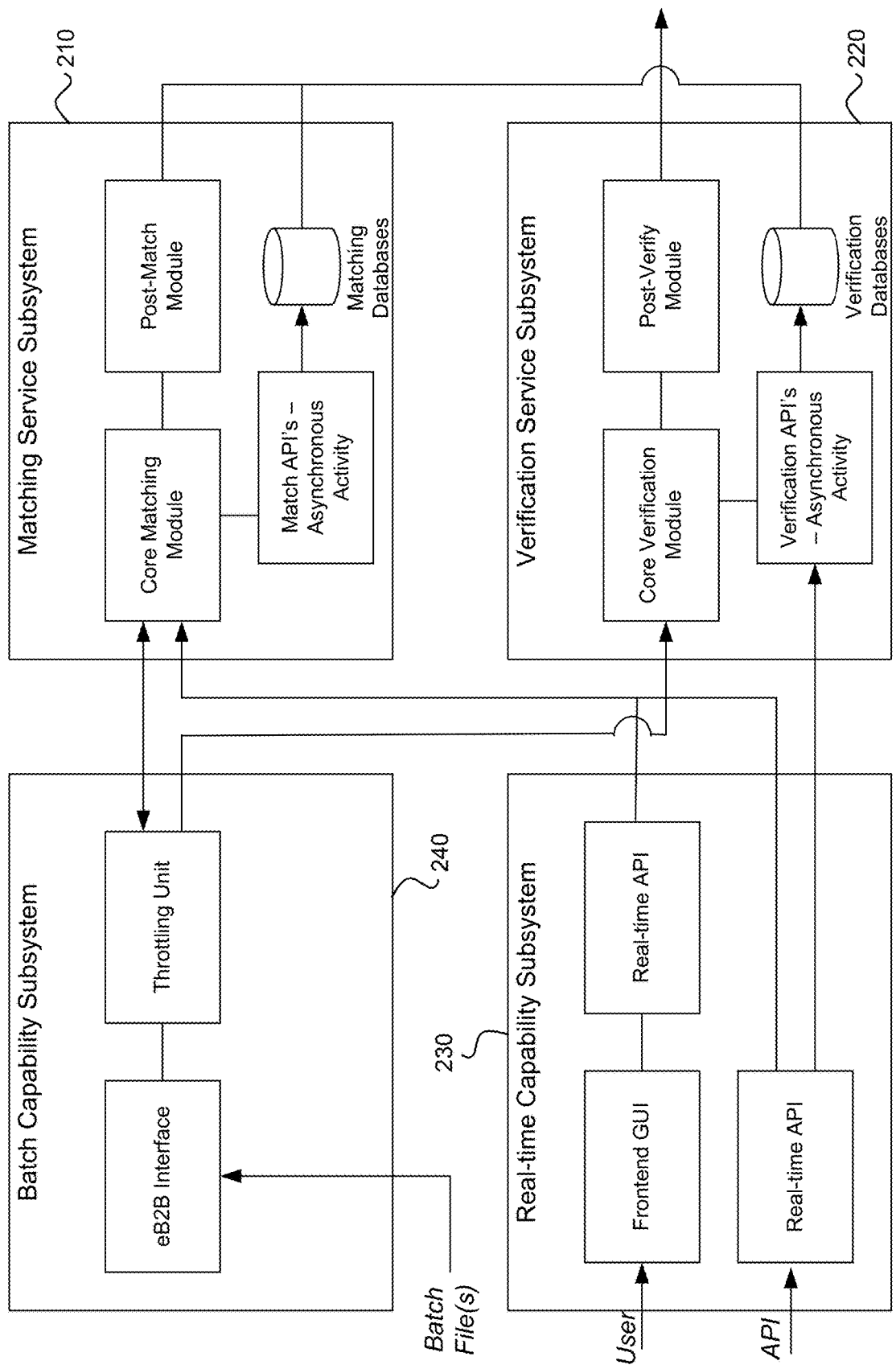
FIG. 2 illustrates an exemplary architecture of an example embodiment of the data processing system shown in FIG. 1.

FIG. 2 illustrates the architecture of an example embodiment of the data processing system shown in FIG. 1. The architectural diagram of FIG. 2 depicts example subsystems of the data processing system to provide core matching and verifications capabilities, which can be implemented as de-coupled micro-services provided to the client computers. For example, such micro-services can be provided as matching and/or verification interfaces, e.g., through the API, operated on the client computer. As shown in FIG. 2, the data processing system includes a batch capability subsystem 240, a real-time or near real-time capability subsystem 230, a matching service subsystem 210 and a verification service subsystem 220.

The batch capability subsystem 240 includes an eB2B interface that receives a batch of records (data) in a file (e.g., on a periodic or aperiodic basis) from the client computer. The eB2B interface provides a file exchange system facilitated by the data processing system exclusive with subscribed clients. The eB2B interface includes a software framework operable to distribute storage and processing of 'big data' datasets. In implementations of file transfers through the eB2B interface, the data goes through a series of validation checks at file and record level and then records are processed by trickling them through the micro-services and finally consolidated into a single output file and sent back to the client through the same eB2B interface. The batch capability subsystem includes a throttling unit to control the number of simultaneous transactions across batch and API mechanism to govern performance.

The real-time or near real-time capability subsystem 230 includes two interfaces, e.g., a front-end GUI and an API. The front-end GUI provides the client computer with a GUI where a client user can input a record at a certain time and submit to the data processing system to implement the match/verify process and receive a response output. The API facilitates the client computer to directly invoke an API exposed and receive the response output in real-time or near real-time.

The batch capability subsystem 240 and the real-time or near real-time capability subsystem 230 can be operated separately or in parallel by the data processing system. Based on the implementation, the batch capability subsystem and/or the real-time or near real-time capability subsystem are in communication with the two main processing subsystems of the data processing system: (i) the matching service subsystem 210 (also referred to as Matching As A Service (MAAS)), and (ii) the verification service subsystem 220 (also referred to as Verification As a Service (VAAS)).

The matching service subsystem 210 provides matching functionality that matches the input/incoming demographic record against records stored in a database of the data processing system, e.g., one or more National Eligibility Databases (NEDBs), and uncovers any other coverage/benefits. The matching service subsystem includes a core matching module which gives match pairs that goes through a secondary process called as post-match process implemented by a post-match module. In post-match process the match pairs undergo a series of rigorous tests to further validate the match accuracy and drops any that doesn't meet the criteria. For example, a post-match rules module can take all of the match result sets and apply specific logic and level rules that will validate match result sets. In some implementations, only those matches that undergo a post-match process will be delivered to the client computer.

The verification service subsystem 220 provides services to verify the identified eligibility from the matching process by making real-time or near real-time communications (e.g., data exchanges, calls, etc.) to the Insurance provider(s) and other data sources to confirm the member/patient's eligibility. This is a pipe line that can include a pre-verification process and a post verification process. Pre-verification process includes a set of rules to determine if an external verification call should be made or not, certain records get dropped at this stage. Post-verification process can include a further set of rules, which based on response from the insurance carrier, determines whether or not to deliver the policy information back to the clients or queue it up for any further process as required. Both of these rule processes can be processed transiently in real-time or near real-time.

In some embodiments, the matching service subsystem 210 and the verification service subsystem 220 are micro services that may be deployed independently without comprising the integrity of the application. Each of these services may be implemented using a web services framework based on a model-view-controller (MVC) design pattern (e.g., Spring REST) with a dedicated database.

The matching service subsystem 210 may include a rules-based engine that can be customized to the requirement of each client and improve the quality of the match. Furthermore, leveraging an in-memory relational database management system (RDBMS) to cache the data reduces the overall processing time and improves overall performance. For example, using the in-memory RDBMS avoids repeated calls to the back-end databases, thereby reducing processing time, and enabling real-time or near real-time operation of the matching and verification processes. The verification service subsystem 220 may also include a business rule management system (BRMS), which incorporates an inference-based rules engine, and that may be customized to the requirements of each healthcare carrier.

The frontend GUI of the real-time or near real-time capability subsystem 230 may be implemented using a scripting language-based frontend web application framework and offers visual representation of data using a library for interactive data visualizations in web browsers. Users may submit member information to match and verify eligibility through the real-time or near real-time capability subsystem 230. The subsystems shown in FIG. 2 exchange data with each other using a data format for asynchronous communication to ensure real-time or near real-time operation and minimal internal communication delays.

Figure 3:
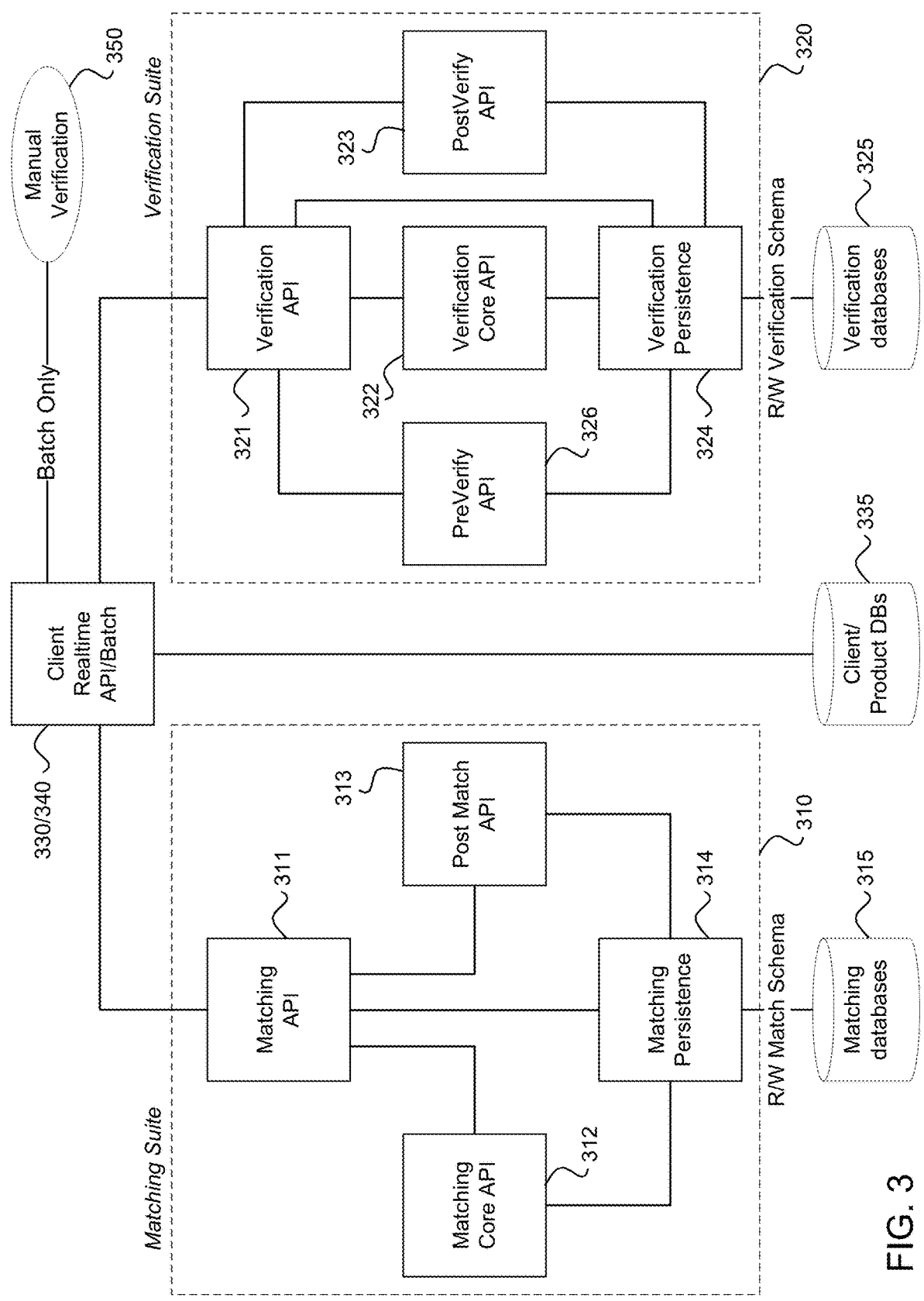
FIG. 3 illustrates an example embodiment of the API operable on the client computer to provide the microservices in accordance with the presently disclosed technology.

FIG. 3 illustrates an example embodiment of the API operable on the client computer to provide the microservices in accordance with the present technology, e.g., through an application on the client computer. As depicted in the diagram, incoming requests are received by the top orchestration aspect of the API (e.g., shown as the Client real-time or near real-time API/Batch subsystem 330/340). From here, the requests are distributed further among the available API's within matching and verification domains, e.g., the matching service subsystem 310 and verification service subsystem 320, respectively.

Matching Domain. In the matching domain, the Matching API 311 sequences the incoming requests by first invoking the Matching Core API 312 which does the core matching and well as performing third-party interactions (when required). The results are then passed to the Post Match API 313 which applies custom rules to filter out matching that does not meet a predefined threshold. In an example, the client information request may be incomplete (or only include partial information), which may result in the Matching Core API finding approximately 20 results that are possible matches, but which are then winnowed down to 1-2 matches after processing by the Post Match API 313. Throughout the process, the Matching Persistence module 314 is invoked to persist the request/result/and filtered result sets of the data to the database 315 in the data processing system. As described earlier, using a data format for asynchronous communication (e.g., JSON) enables different fields to be parsed without requiring changes to the database structure.

Verification Domain. In the verification domain, the Verification API 321 sequences the incoming requests (e.g., which could be output from post-match API or a direct verification request from client computer without match) by first invoking the PreVerify API 326 which applies certain rules to see if a verification is even required or not, then the Verification Core API 322 is invoked which actually sends the request (e.g., an EDI 270 transaction) out to carriers to check eligibility and receives the response (e.g., an EDI 271 transaction), and then finally invokes the PostVerify API 323 to reapply previously run and additional rules to validate carrier response data as it may have changed during the verification to ensure that the now verified data remains valid for delivery. Throughout the verification process, the Verification Persistence module 324 records outputs to the back-end database 325. In some embodiments, the PreVerify API 326 parses and reformats the incoming requests to match a format required by the healthcare carrier that the verification request is destined for.

Figure 4:
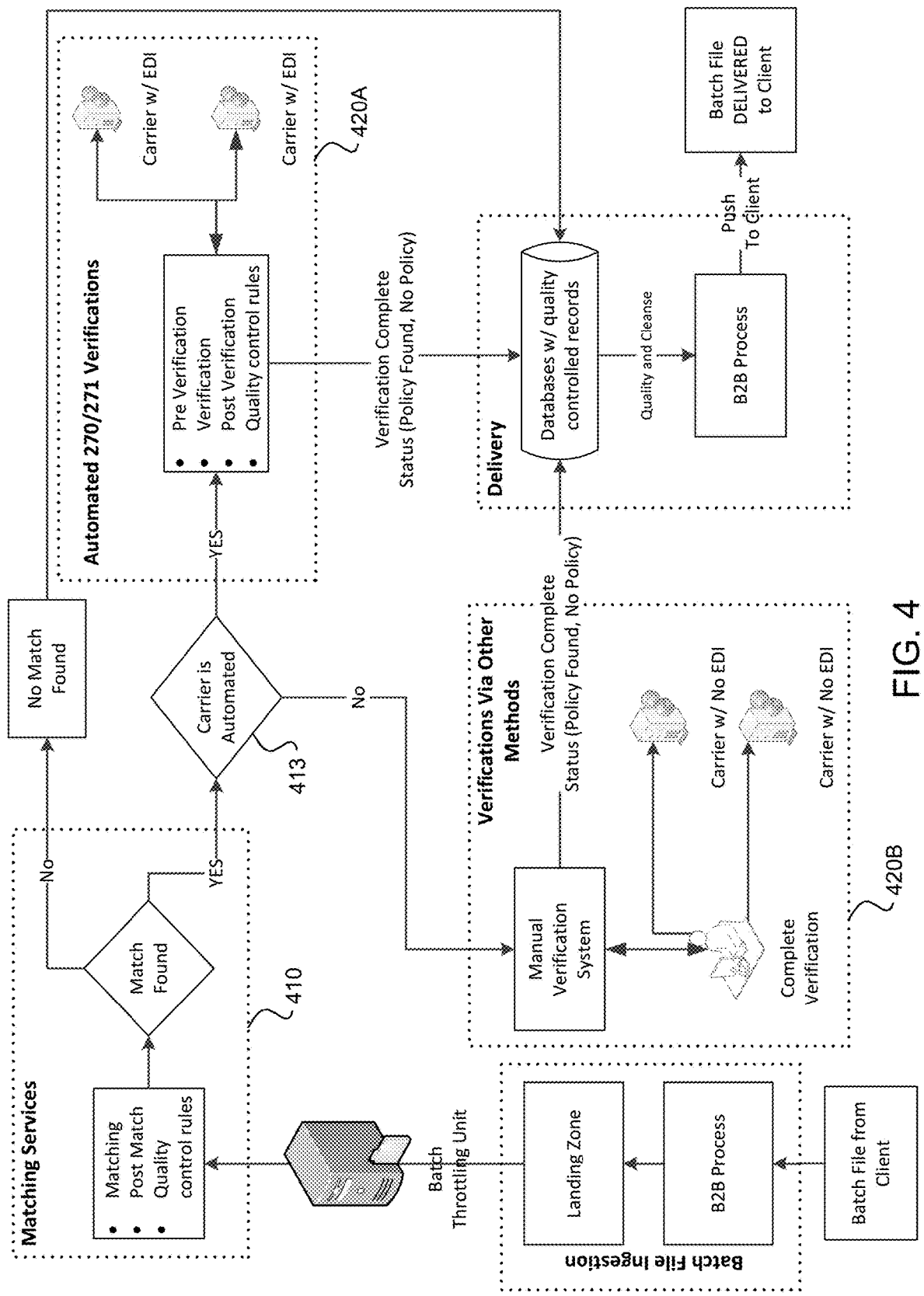
FIG. 4 illustrates an exemplary flowchart for batch processing in accordance with the presently disclosed technology.

FIG. 4 illustrates an exemplary flowchart for batch processing in accordance with the presently disclosed technology. As shown therein, when a batch file is received is it first parsed (and optionally throttled, if required) prior to processing by the matching services 410, which operates as described earlier for the Matching Domain 310 in FIG. 3. The parsing of the input batch file by the Batch File Ingestion process includes reading records from the input file in which the fields are pipe delimited (e.g., "|"), comma-separated, fixed-width columns, etc., validating the records and writing the records to one or more tables in a database. In an example, a record in the input batch file may be specified using a number of alphanumeric fields, e.g., the fields shown in FIGS. 9A and 9B.

If a match is found, the process determines whether the healthcare carrier is enabled to provide automated processing. It automation is available ("YES" at 413), the process continues to the automated 270/271 verifications (420A) that includes functionality similar to that described for the Verification Domain 320 in FIG. 3. The 270/271 verifications are indicative of the electronic data interchange (EDI) inquiry and response transactions, which are standardized methods to communicate eligibility and benefit information between healthcare providers and insurance companies. In the event that automation is not available ("NO" at 413), the matched records are sent for verification via other methods (420B), which includes manual verification via phone or carrier portal. Upon completing verification using either method (420A or 420B), the coverage and/or policy information is delivered to the client in response to the batch file request. In some embodiments, the process may filter out duplicate records that were present in the input batch file when responding to the client batch request.

Figure 5:
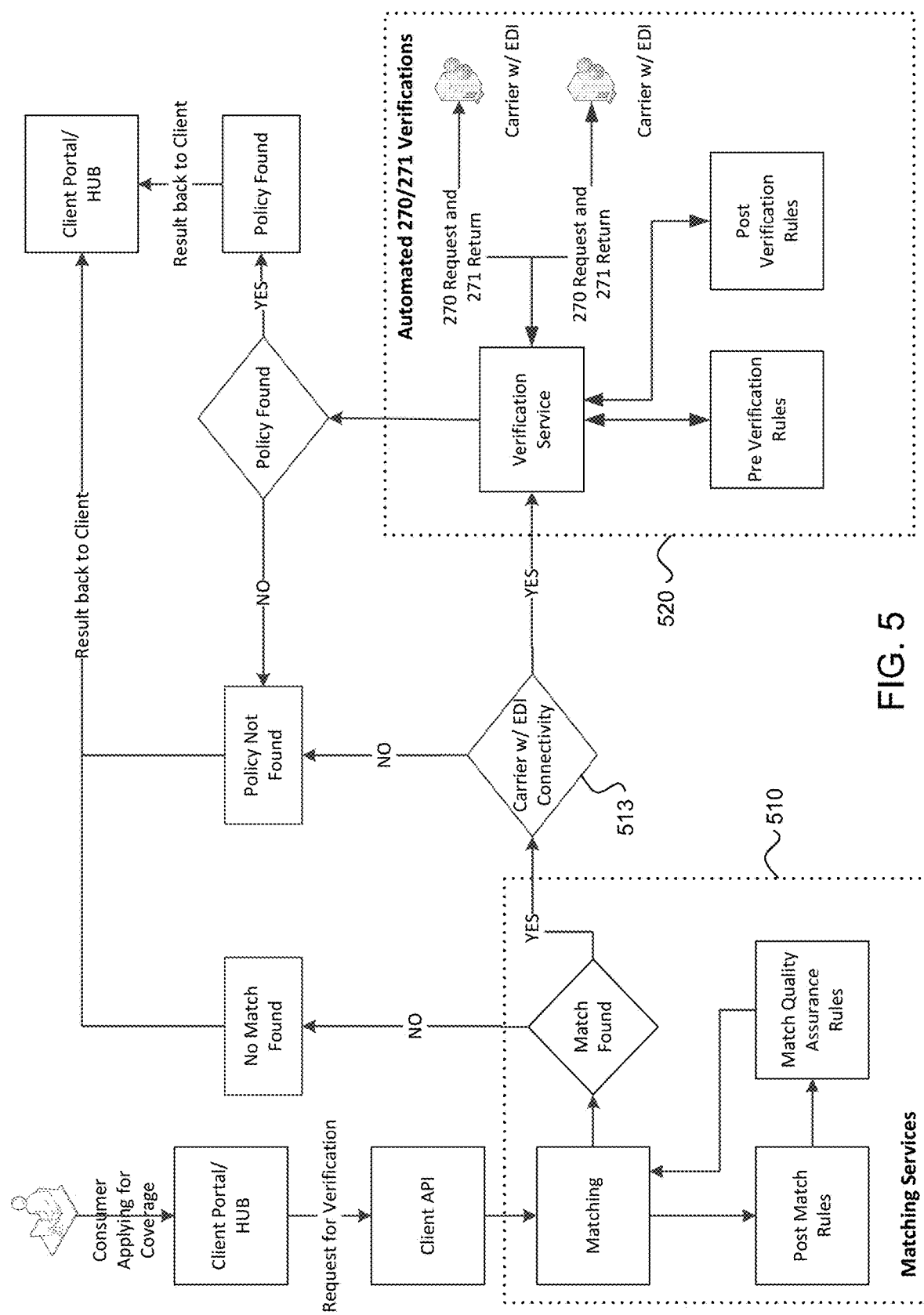
FIG. 5 illustrates an exemplary flowchart for online real-time or near real-time processing in accordance with the presently disclosed technology.

FIG. 5 illustrates an exemplary flowchart for online real-time or near real-time processing in accordance with the presently disclosed technology. This example includes some features and/or operations that are similar to those shown in FIG. 4, and described above. At least some of these features and/or components may not be separately described in this section. The process begins with a client applying for coverage via the client portal and API (with functionality similar to the frontend GUI and API of the real-time or near real-time capability subsystem 230 in FIG. 2), which is then processed by the matching services 510. If a match is found, the process determines whether the healthcare carrier is enabled to provide automated processing. If automation is available ("YES" at 513), the process continues with the automated 270/271 verifications, and the verified coverage and/or policy is delivered to the client. If automation is unavailable ("NO" at 513), the client is informed that the carrier does not support EDI or the carrier is unable to verify the policy at this time (since the process shown in FIG. 5 supports real-time or near real-time processing).

Figure 6:
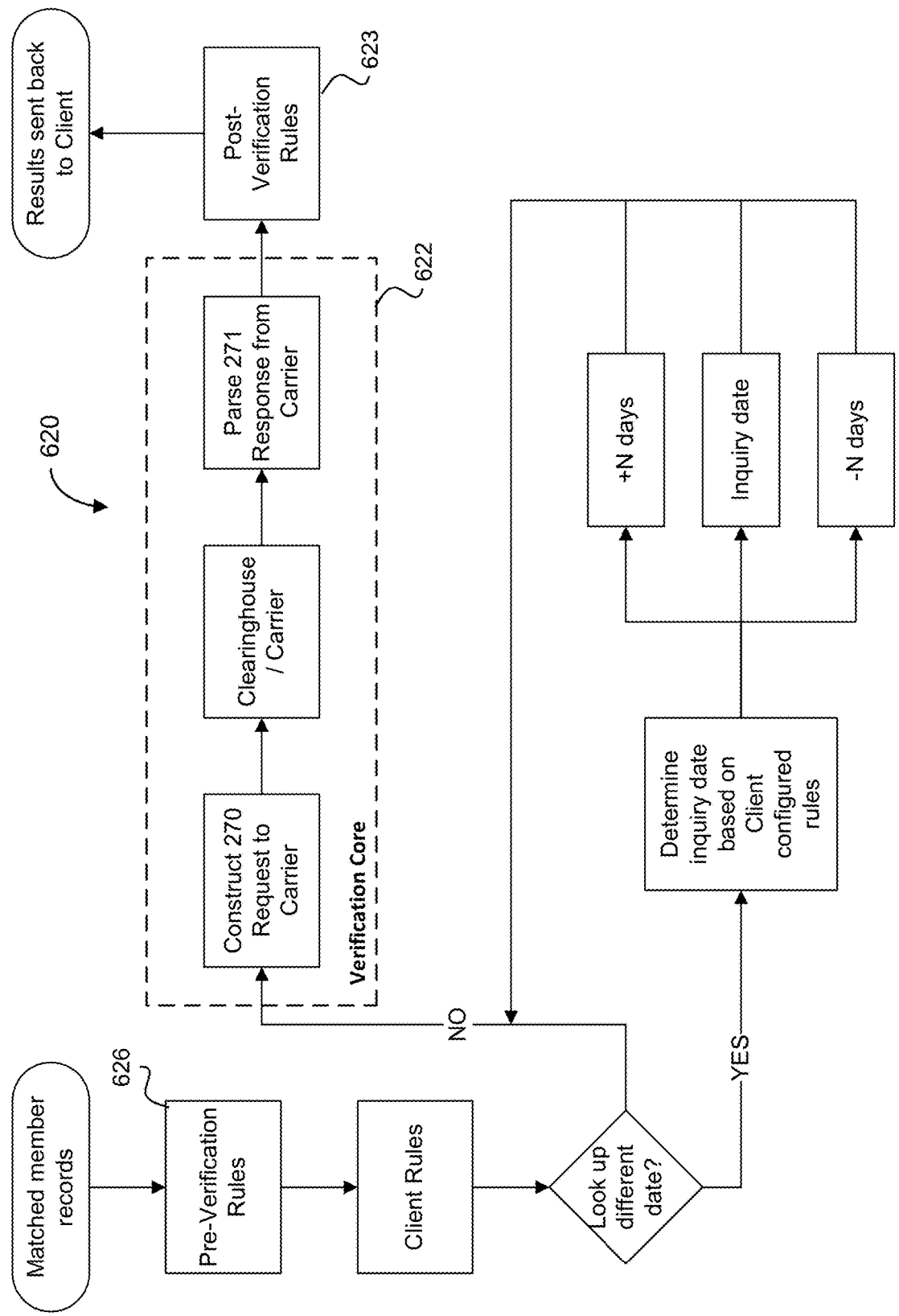
FIG. 6 illustrates an exemplary flowchart for an online verification operation in accordance with the presently disclosed technology.

FIG. 6 illustrates an exemplary flowchart for an online verification operation in accordance with the presently disclosed technology. The online verification operation begins with the input of a matched member record, which is first processed by pre-verification rules 626, which applies certain rules to see if a verification is even required or not, and if it is required, parses and reformats the matched member record to match a format specified by the healthcare carrier that the matched member record is destined for. Custom client rules are then implemented, and followed by a check on whether a different date needs to be examined. In the event of matched policies with insufficient details, pre-defined client rules will allow the system to perform multiple verification check with different inquiry dates (e.g., +/−N days, where N is configurable and may be a default value like 30, 60, 90, 120, or a specific value selected based on client specifications) to the carrier systems to fetch more detailed and appropriate information about policies. The verification core 622 then constructs an EDI 270 transaction to send to the carrier, and receives an EDI 271 transaction in response. In some embodiments, the matched member record that is received as input may have information (e.g., complete or incomplete fields) that does not exactly match the format of the EDI 270 transaction, and the verification core 622 reformats (using, for example, a rules-based engine) the record to the required format. The received EDI 271 transaction is then processed by post verification rules 623 before the results are sent back to the client.

In some embodiments, a client may be covered by multiple carriers, which may be determined from the matched member record including multiple carrier codes. In this scenario, the online verification operation will generate multiple EDI 270 inquiry transactions, each one customized to the specific carrier that is being contacted. An EDI 271 response transaction is received for each EDI 270 inquiry transaction, and each of the responses processed by post verification rules 623 prior to combining the results for delivery to the client. In another example, the responses from the multiple carriers could be delivered individually to the client.

Figure 7:
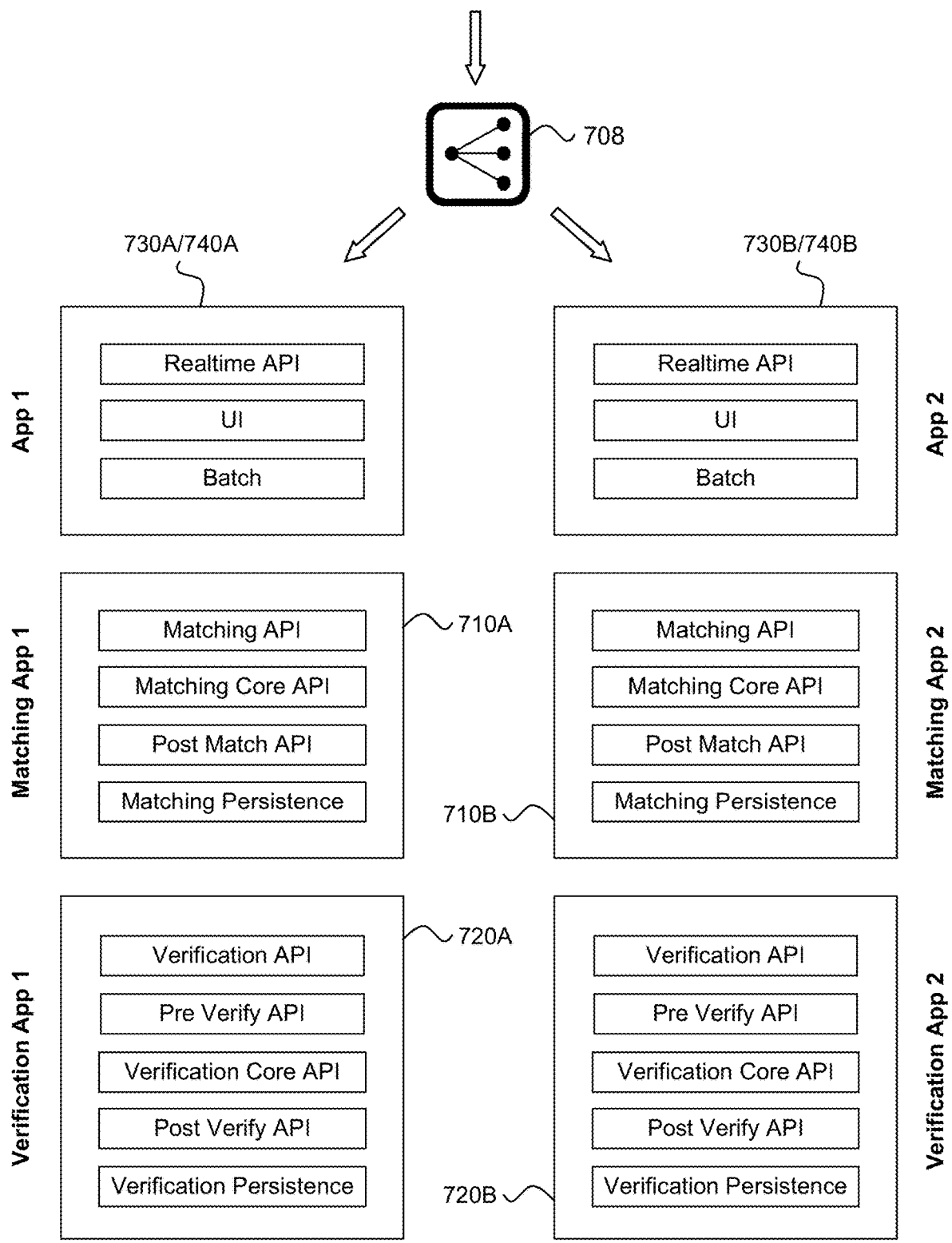
FIG. 7 illustrates an example implementation of an application that can be implemented on the client computer in communication with the data processing system.

FIG. 7 illustrates an example of a physical deployment architecture of an application that can be implemented on the client computer in communication with the data processing system. As shown in the diagram, redundancy is built in to the architecture of the application to handle high availability. Requests go through a network load balancer 708 and are load balanced between the two instances that are always in active-active mode. This enables the application to handle requests even if one of the instances is down. For example, the first WebLogic App pair of instances (730A/740A and 730B/740B) takes care of exposing the core interfaces, e.g., solution subsystem. The application server Matching App instances (710A and 710B) provide the matching micro-service and also the post-match logic that filters the matched records based on our proprietary algorithms/rules. The application server Verification App instances (720A and 720B) host the verification subsystem and also include the hooks to run custom rules for pre verification and post verification stages.

Figure 8:
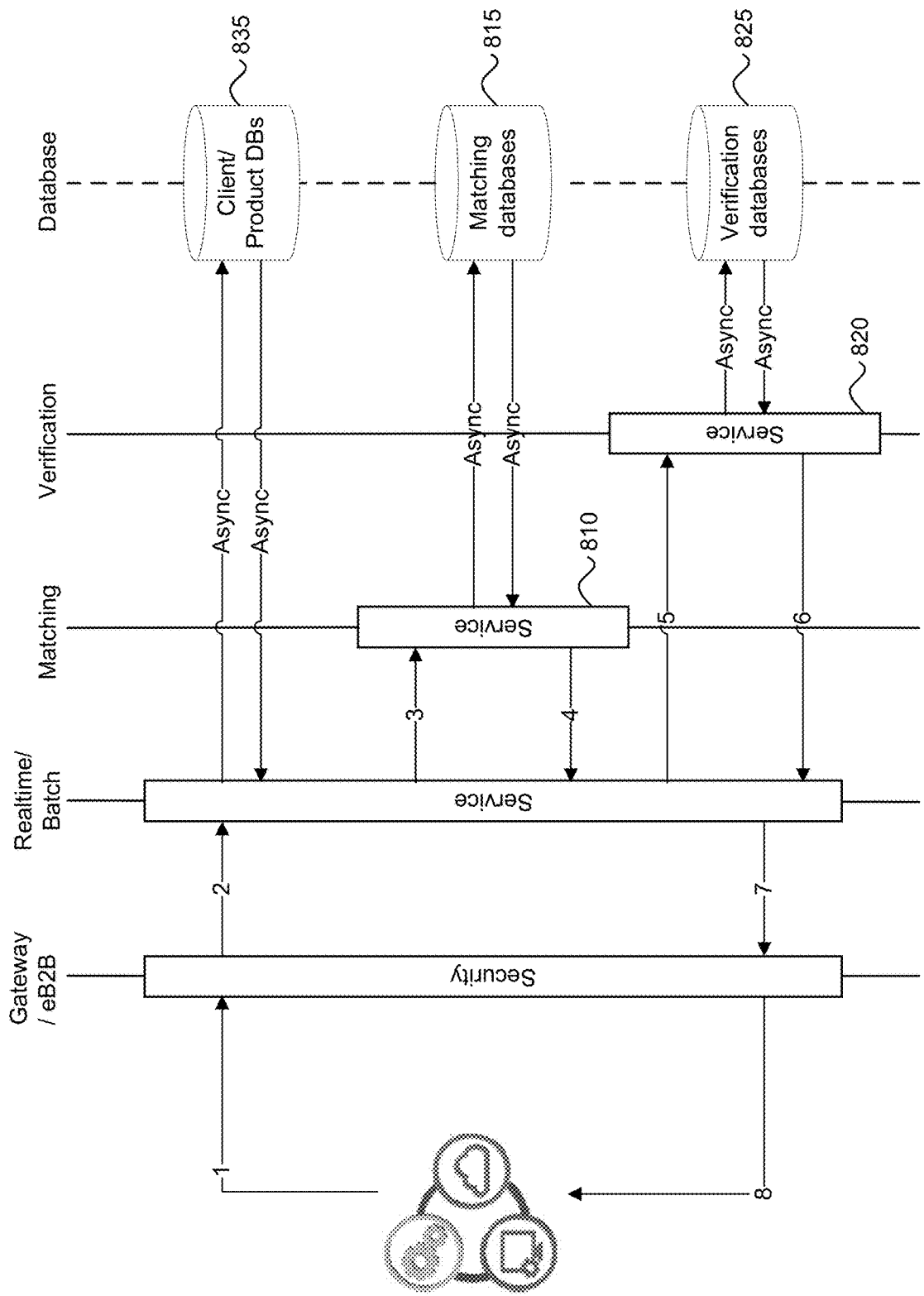
FIG. 8 illustrates an example flow and sequence of data through an example stack/components of the data processing system.

FIG. 8 shows a diagram depicting the flow and sequence of a request through an example stack/components of the data processing system. As shown in the diagram, the requests originate externally (e.g., on client side either through API/Batch/UI) to the data processing system and hits the external facing security layer of the data processing system (e.g., included in the eB2B subsystem), which is an API Gateway or eB2B which exposes a secure file transfer interface (denoted as operation "1"). From there the request passes through a series of micro-services the first one is a real-time or near real-time/batch service (operation "2") which orchestrates the incoming requests and further passes through matching service 810 (operations "3" and "4") and verification service 820 (operations "5" and "6"). The response is then delivered, through the external facing security layer (operation "7"), to the client (operation "8"). In some implementations, throughout the process shown in FIG. 8, outputs are recorded asynchronously to the backend persistent layer (databases 835, 815 and 825).

FIGS. 9A and 9B illustrate example request and response parameters that may be used in conjunction with the embodiments described in FIGS. 2-8. In some embodiments, the request parameters shown in FIG. 9A may be used in the matching component. For example, the post-match component (or API) may use criteria that include a member social security number (SSN), a date of birth (DOB) and an address for validation. In other embodiments, the response parameters shown in FIG. 9B may be used by the post-verify component (or API) to verify that the response is still valid and may be delivered to the client (or user).

Figure 10:
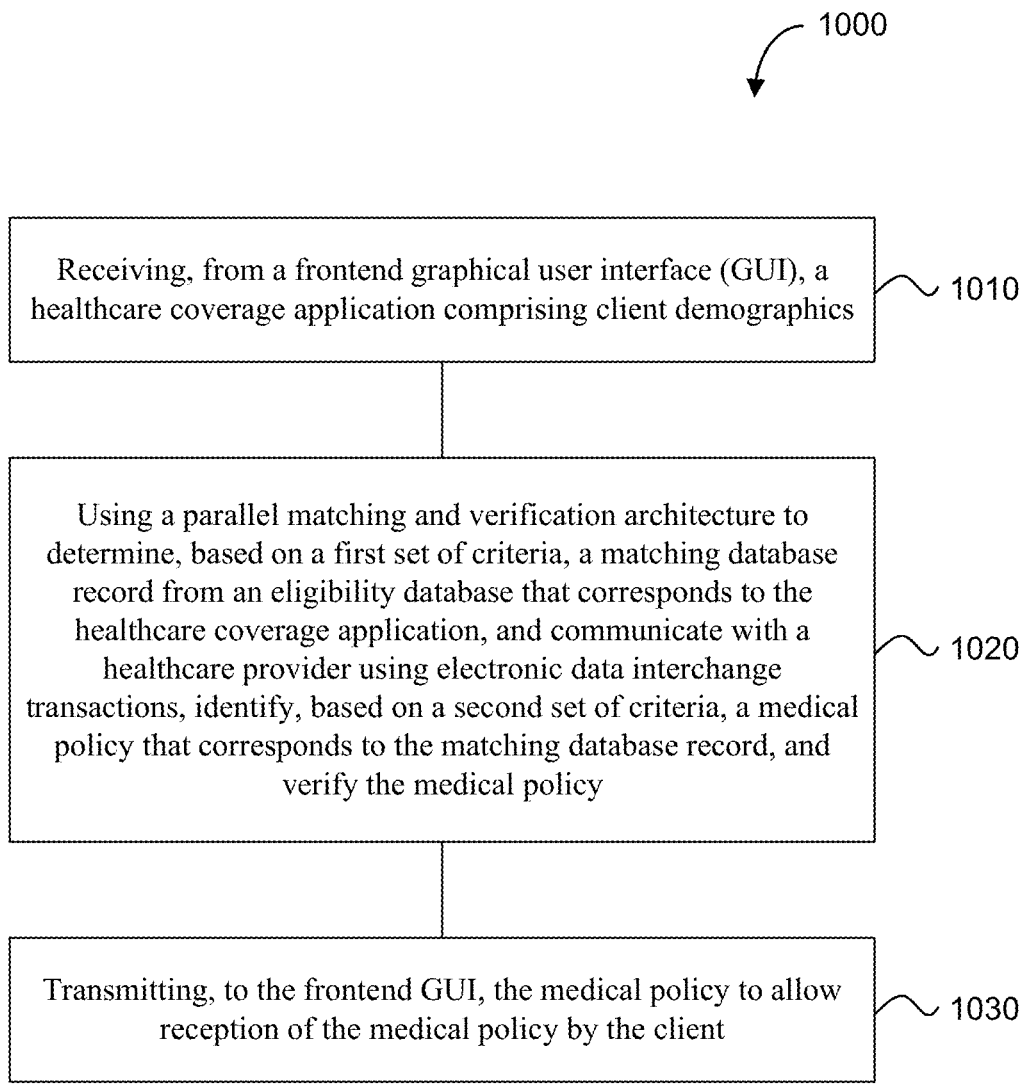
FIG. 10 illustrates a flowchart of a method for healthcare coverage matching and verification in accordance with the presently disclosed technology.

FIG. 10 illustrates a flowchart of a method 1000 for healthcare coverage matching and verification in accordance with the presently disclosed technology. The method 1000 includes, at operation 1010, receiving, from a frontend graphical user interface (GUI), a healthcare coverage application comprising client demographics. In some embodiments, the client demographics include multiple combinations of the following: a last name, a first name, a birthdate, an identification number, an address and a request type associated with a client. In other embodiments, the client demographics may include other parameters including the request parameters enumerated in FIG. 9A. In yet other embodiments, the client demographics include one or more demographic details, such that using additional demographic details increase the accuracy of the matching and verification processes described in this document.

The method 1000 includes, at operation 1020, using a parallel matching and verification architecture to determine, based on a first set of criteria, a matching database record from an eligibility database that corresponds to the healthcare coverage application, and communicate with a healthcare provider using electronic data interchange (EDI) transactions, identify, based on a second set of criteria, a medical policy that corresponds to the matching database record, and verify the medical policy.

In some embodiments, and as described in the context of the matching component in FIGS. 2-8, determining the matching database record includes matching, based on the first set of criteria, multiple database records in the eligibility database, and performing a refinement operation on the multiple database records, based on a third set of criteria, to determine the matching database record. In an example, the first set of criteria may be selected from the request parameters illustrated in FIG. 9A.

In some embodiments, and as described in the context of the verification component in FIGS. 2-8, identifying the medical policy includes processing, prior to the identifying, the matching database record to be compatible with the EDI transactions, and determining whether the medical policy is valid for reception of the medical policy by the client. In an example, the validation and verification of the medical policy may be based on one or more of the response parameters illustrated in FIG. 9B.

In some embodiments, the EDI transactions comprise an EDI 270 inquiry transaction and an EDI 271 response transaction.

The method 1000 includes, at operation 1030, transmitting, to the frontend GUI, the medical policy to allow reception of the medical policy by the client.

In some embodiments, each message to and from the API of the frontend GUI is intercepted and authenticated by a secure communications component. In an example, the secure communications component may use a JSON Web Token (JWT), which is a compact URL-safe means of representing claims to be transferred between two parties.

Figure 11:
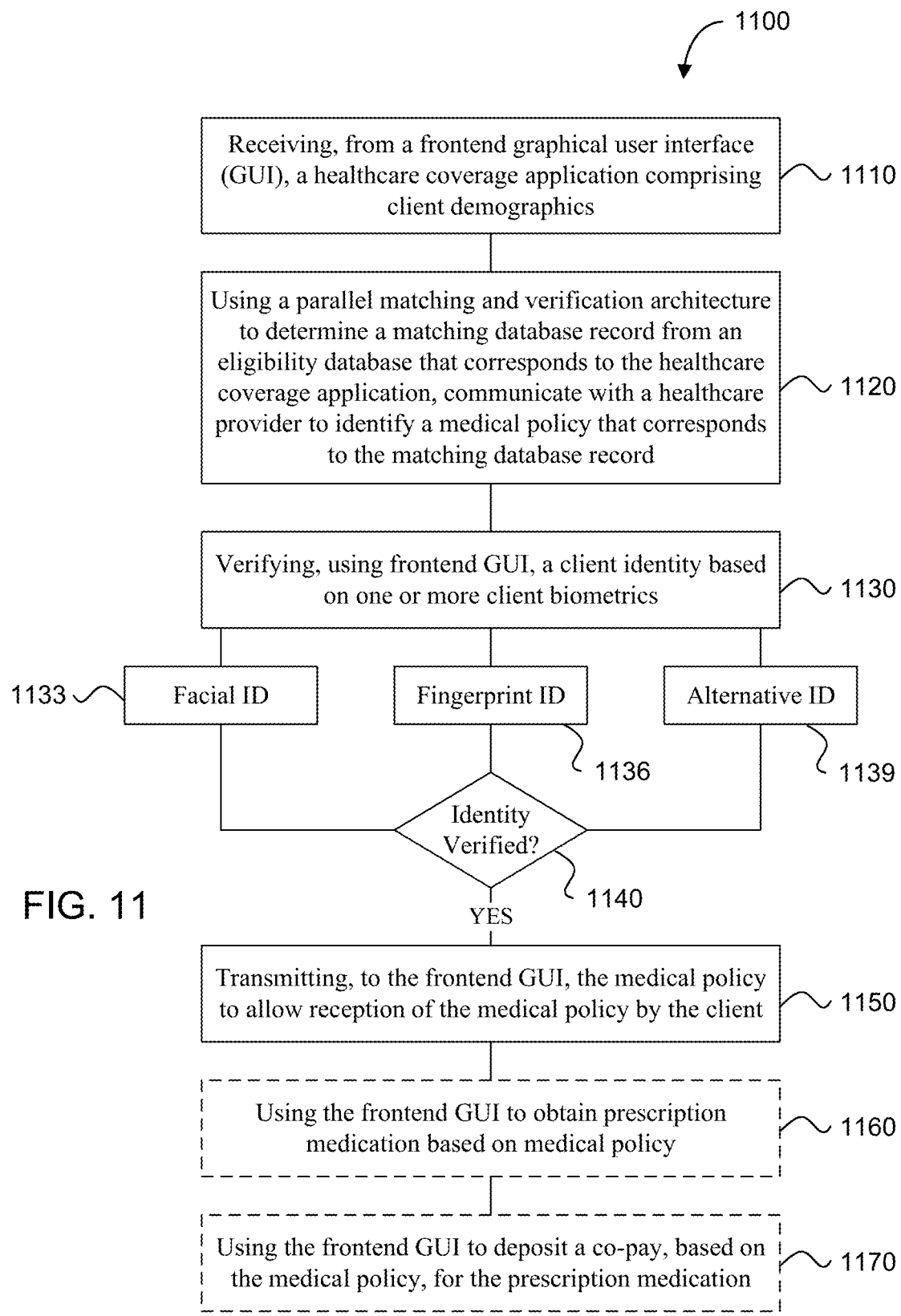
FIG. 11 illustrates a flowchart for another method for healthcare coverage matching and verification in accordance with the presently disclosed technology.

FIG. 11 illustrates a flowchart of another method 1100 for healthcare coverage matching and verification in accordance with the presently disclosed technology. The method 1100 includes, at operation 1110, receiving, from a frontend graphical user interface (GUI), a healthcare coverage application comprising client demographics. In some embodiments, the client demographics may include multiple combinations of fields described in FIGS. 9A and 9B. In other embodiments, the client demographics may further include one or more identifiers that uniquely identify the client.

The method 1100 includes, at operation 1120, using a parallel matching and verification architecture (as described, for example, in FIGS. 3 and 8) to determine a matching database record from an eligibility database that corresponds to the healthcare coverage application, communicate with a healthcare provider to identify a medical policy that corresponds to the matching database record. In some embodiments, the eligibility database may be supported by the healthcare provider. In other embodiments, it may be supported by a third party (e.g., the United States government) distinct from the healthcare provider.

The method 1100 includes, at operation 1130, verifying, using frontend GUI, a client identity based on one or more client biometrics. In some embodiments, client identity verification ensures that communication between a remote terminal (or client-facing application) is not unnecessarily performed if, in fact, the client's identity has been compromised. In other embodiments, the client identity verification may occur prior to delivering the results to the person (or persons) using the remote terminal (or client-facing application).

For example, a facial ID (1133) or a fingerprint ID (1136) may be used to verify the client's identity. In some embodiments, the facial ID may be coordinated with existing face recognition implementations (similar to, for example, signing in to websites with other social media accounts). In other embodiments, an alternative ID (1139), e.g. government-issued identification verification like E-Verify, SENTRI or NEXUS supported by the Department of Homeland Security, may be used in if the facial or fingerprint ID are not available in a specific client application being used.

The method 1100 includes, at operation 1140, the client identity is verified.

The method 1100 includes, at operation 1150, and upon verification of the client identity, transmitting the medical policy to the frontend GUI to allow reception of the medical policy by the client. In some embodiments, the transmission may also be send to a mobile device or to a pharmacy designated by the client, if any medication needs to be collected by the client.

The method 1100 includes, at operation 1160, using the frontend GUI to obtain prescription medication based on medical policy. In an example, the client may be provided with specific instructions and warnings related to the prescription medication through the frontend GUI, and may optionally require the client to passively (e.g., a signature) or actively (e.g., one or more questions) acknowledge understanding of the specific instructions and warnings. The prescription medication may be dispensed only after client acknowledgement.

The method 1100 includes, at operation 1170, using the frontend GUI to deposit a co-pay, based on the medical policy, for the prescription medication. In some embodiments, payment of the co-pay may be associated with the facial ID and linked to one or more credit cards or other funding sources belonging to the client, or a trusted source of the client. In other embodiments, the frontend GUI may accept a cash payment.

Figure 12:
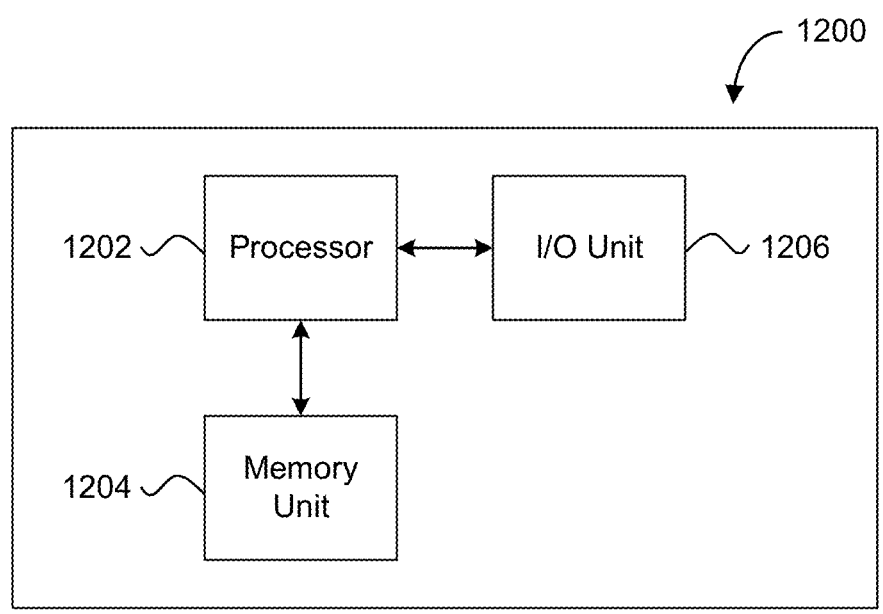
FIG. 12 illustrates an example embodiment of a data processing device of a data processing system and/or a client computer that may implement the presently disclosed technology.

FIG. 12 shows a block diagram of an example embodiment of a data processing device 1200 of a data processing system and/or a client computer that implements the disclosed technology. The data processing device includes a processor 1202 in communication with a memory unit 1204 and an input/output (I/O) unit 1206. The processor 1202 is configured to process data, and the memory unit 1204 is in communication with the processor to store and/or buffer the data. To support various functions of the data processing device, the processor can be included to interface with and control operations of other devices, e.g., via the I/O unit 1206.

In various implementations, the processor 1202 can include one or more processors, e.g., including but not limited to microprocessors such as a central processing unit (CPU), microcontrollers, or the like. The memory unit 1204 can include and store processor-executable code, which when executed by the processor, configures the data processing device to perform various operations, e.g., such as receiving information, commands, and/or data, processing information and data, and transmitting or providing information/data to another device. The memory unit can store other information and data, such as instructions, software, values, images, and other data processed or referenced by processor. For example, various types of Random Access Memory (RAM) devices, Read Only Memory (ROM) devices, Flash Memory devices, and other suitable storage media can be used to implement storage functions of memory unit. The memory unit can store healthcare data and information, e.g., including patient medical data, insurance information, and healthcare cost information, which can be used in the implementation of the techniques in accordance with the present technology. In some implementations, the data processing device includes an input/output unit (I/O) 1206 to interface the processor and/or memory unit to other modules, units or devices associated with the system, and/or external devices. For example, the I/O unit can connect to an external interface, source of data storage, or display device. Various types of wired or wireless interfaces compatible with typical data communication standards, such as Universal Serial Bus (USB), IEEE 1394 (FireWire), Bluetooth, Bluetooth low energy (BLE), ZigBee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces, can be used to communicate data with the data processing device via the I/O unit. In some implementations, for example, the data processing device 1200 includes a wireless communications unit, e.g., such as a transmitter (Tx) or a transmitter/receiver (Tx/Rx) unit. In such implementations, for example, the I/O unit can interface the processor and memory unit with the wireless communications unit to utilize various types of wireless interfaces, such as the examples described above. The I/O unit can interface with other external interfaces, sources of data storage, and/or visual or audio display devices, etc. to retrieve and transfer data and information that can be processed by the processor, stored in the memory unit, or exhibited on an output unit of a user device (e.g., display screen of a computing device) or an external device.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing system", "data processing unit", and/or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for facilitating processing of medical information, comprising:
    a user interface to receive a healthcare claim comprising client demographics associated with a client;
    a first processor communicatively coupled to the user interface; and
    a second processor communicatively coupled to the user interface,
    wherein a matching component is implemented in the first processor, wherein the first processor executes instructions to process the client demographics in the healthcare claim, access a matching database and determine a matching database record that corresponds to the healthcare claim,
    wherein a verification component is implemented in the second processor, wherein the second processor executes instructions to communicate with one or more coverage providers, identify coverage information that corresponds to the matching database record, and verify the coverage information in a verification database,
    wherein the system is configured to perform a coordination of benefits operation between the one or more coverage providers upon a determination that the coverage information comprises an indication that the client has coverage from at least two coverage providers,
    wherein the matching component and the verification component are implemented as separate and independently configurable components to enable their separate and concurrent usage, and are communicatively connected to the user interface in a parallel configuration,
    wherein the second processor executes the instructions to process a first healthcare claim at substantially same time as the first processor executes the instructions to process a second healthcare claim that is subsequent to the first healthcare claim,
    wherein the second processor executes the instructions to communicate with the one or more coverage providers using transactions with a predetermined format.

2. The system of claim 1, wherein the matching component and the verification component are enabled to asynchronously access their respective databases.

3. The system of claim 1, further comprising:
    a secure communications component, communicatively connected to the user interface, to intercept and authenticate each message to and from an application program interface (API) of the user interface.

4. The system of claim 1, wherein the matching component comprises:
    a matching core, communicatively connected to the user interface, to match, based on a first set of criteria, multiple database records in the matching database; and
    a post-match component, communicatively connected to the matching core, to perform a refinement operation on the multiple database records, based on a second set of criteria, to determine the matching database record.

5. The system of claim 1, wherein the predetermined format is an electronic data interchange (EDI)-compatible format.

6. The system of claim 5, wherein the verification component comprises:
a pre-verification component, communicatively connected to the user interface, to process the matching database record to be compatible with the transactions;
a verification core, communicatively connected to the pre-verification component, to communicate with a healthcare provider; and
a post-verification component, communicatively connected to the verification core and the user interface, to determine whether the coverage information is valid for subsequent payment of the healthcare claim by the at least two coverage providers.

7. The system of claim 5, wherein the transactions comprise an EDI 270 inquiry transaction and an EDI 271 response transaction.

8. A method for facilitating processing of medical information, comprising:
receiving, from a frontend graphical user interface (GUI), a batch file comprising a plurality of healthcare coverage applications, each healthcare coverage application comprising client demographics associated with a corresponding client, wherein a format of a first healthcare coverage application is different from a format of a second healthcare coverage application;
using a parallel matching and verification architecture to:
perform a matching operation to determine a matching database record from a matching database that corresponds to each of the plurality of healthcare coverage applications,
perform a reformatting operation to convert a format of at least one healthcare coverage application to an electronic data interchange (EDI)-compatible format, and
perform a verification operation to communicate with a healthcare provider using the EDI-compatible format, identify a medical policy that corresponds to the matching database record, and verify the medical policy in a verification database; and
transmitting, to the frontend GUI, the medical policy to allow reception of the medical policy by the corresponding client,
wherein the matching operation and the verification operation are independently configured to operate separately and concurrently, wherein communicating with the healthcare provider regarding a first healthcare coverage application occurs at substantially same time as determining the matching database record for a second healthcare coverage application that is received subsequent to the first healthcare coverage application, and
wherein communicating with the healthcare provider comprises using the EDI-compatible format.

9. The method of claim 8, further comprising:
perform, based on a performance of the parallel matching and verification architecture, a throttling operation on the batch file.

10. The method of claim 8, wherein the matching operation and the verification operation are enabled to asynchronously access their respective databases.

11. The method of claim 8, further comprising:
filtering out a duplicate healthcare coverage application from the batch file.

12. The method of claim 8, wherein determining the matching database record comprises:
matching, based on a first set of criteria, multiple database records in the matching database; and
performing a refinement operation on the multiple database records, based on a second set of criteria, to determine the matching database record.

13. The method of claim 8, wherein the parallel matching and verification architecture comprises (a) a matching component configured to perform the matching operation and (b) a verification component configured to perform the reformatting and verification operations.

14. A system for facilitating processing of medical information, comprising:
a frontend graphical user interface (GUI) to receive a batch file comprising a plurality of healthcare coverage applications, each healthcare coverage application comprising client demographics associated with a corresponding client, wherein a format of a first healthcare coverage application is different from a format of a second healthcare coverage application;
a first processor communicatively coupled to the frontend GUI; and
a second processor communicatively coupled to the frontend GUI,
wherein a matching component is implemented in the first processor and configured to perform a matching operation to determine a matching database record from a matching database that corresponds to each of the plurality of healthcare coverage applications,
wherein a verification component is implemented in the second processor and configured to perform a reformatting operation to convert a format of at least one healthcare coverage application to an electronic data interchange (EDI)-compatible format, perform a verification operation to communicate with a healthcare provider using the EDI-compatible format, identify a medical policy that corresponds to the matching database record, verify the medical policy in a verification database, and transmit, to the frontend GUI, the medical policy to allow reception of the medical policy by the corresponding client,
wherein the matching operation and the verification operation are independently configured to operate separately and concurrently, and wherein communicating with the healthcare provider regarding a first healthcare coverage application occurs at substantially same time as determining the matching database record for a second healthcare coverage application that is received subsequent to the first healthcare coverage application.

15. The system of claim 14, further comprising:
a throttling unit, communicatively connected to the first processor and the second processor, to perform, based on a performance of the matching operation and the verification operation, a throttling operation on the batch file.

16. The system of claim 14, wherein the matching operation and the verification operation are enabled to asynchronously access their respective databases.

17. The system of claim 14, wherein a duplicate healthcare coverage application is filtered out from the batch file.

18. The system of claim 14, wherein the matching component is configured, as part of determining the matching database record, to:
match, based on a first set of criteria, multiple database records in the matching database; and perform a refinement operation on the multiple database records, based on a second set of criteria, to determine the matching database record.

19. A method for facilitating processing of medical information, comprising:
   receiving, using a user interface, a healthcare claim comprising client demographics associated with a client;
   using a matching component to process the client demographics in the healthcare claim, access a matching database, and determine a matching database record that corresponds to the healthcare claim;
   using a verification component to reformat the healthcare claim by converting a format of the healthcare claim to a predetermined format, communicate with one or more coverage providers using the predetermined format, identify coverage information that corresponds to the matching database record, and verify the coverage information in a verification database; and
   performing a coordination of benefits operation between the one or more coverage providers upon a determination that the coverage information comprises an indication that the client has coverage from at least two coverage providers,
   wherein the matching component and the verification component are implemented as separate and independently configurable components to enable their separate and concurrent usage, and are communicatively connected to the user interface in a parallel configuration, and
   wherein the verification component processes a first healthcare claim at substantially same time as the matching component processes a second healthcare claim that is subsequent to the first healthcare claim.

20. The method of claim 19, wherein the matching component and the verification component are enabled to asynchronously access their respective databases.

21. The method of claim 19, further comprising:
   using a secure communications component to intercept and authenticate each message to and from an application program interface (API) of the user interface.

22. The method of claim 19, further comprising:
   using the matching component to match, based on a first set of criteria, multiple database records in the matching database, and perform a refinement operation on the multiple database records, based on a second set of criteria, to determine the matching database record.

23. The method of claim 19, wherein the verification component communicates with the one or more coverage providers using electronic data interchange (EDI) transactions, and wherein the predetermined format is an EDI format.

24. The method of claim 23, further comprising:
   using the verification component to process the matching database record to be compatible with the EDI transactions, communicate with a healthcare provider, and determine whether the coverage information is valid for subsequent payment of the healthcare claim by the at least two coverage providers.

25. The method of claim 23, wherein the EDI transactions comprise an EDI 270 inquiry transaction and an EDI 271 response transaction.

\* \* \* \* \*